United States Patent [19]

Solar

[11] Patent Number: 5,413,560

[45] Date of Patent: May 9, 1995

[54] METHOD OF RAPID CATHETER EXCHANGE

[75] Inventor: Ronald J. Solar, San Diego, Calif.

[73] Assignee: Pameda N.V., Netherlands Antilles

[21] Appl. No.: 966,693

[22] Filed: Oct. 26, 1992

Related U.S. Application Data

[62] Division of Ser. No. 859,220, Mar. 30, 1992.

[51] Int. Cl.⁶ .................. A61M 5/178; A61M 29/00; A61F 2/06
[52] U.S. Cl. ...................... 604/164; 623/1; 604/96; 606/194
[58] Field of Search ............. 606/191–199; 604/96, 164; 623/1

[56] References Cited

U.S. PATENT DOCUMENTS

| | | |
|---|---|---|
| 3,906,938 | 9/1975 | Fleischhacker . |
| 3,973,556 | 8/1976 | Fleischhacker . |
| 4,538,622 | 9/1985 | Samson et al. . |
| 4,545,390 | 10/1985 | Leary . |
| 4,554,929 | 11/1985 | Samson et al. . |
| 4,601,713 | 7/1986 | Fugua . |
| 4,619,274 | 10/1986 | Morrison . |
| 4,719,924 | 6/1988 | Crittenden et al. . |
| 4,757,827 | 7/1988 | Buchbinder et al. . |
| 4,762,129 | 8/1988 | Bonzel . |
| 4,813,434 | 3/1989 | Buchbinder et al. . |
| 4,815,478 | 3/1989 | Buchbinder et al. . |
| 4,820,349 | 4/1989 | Saab . |
| 4,944,740 | 7/1990 | Buchbinder et al. . |
| 4,954,126 | 9/1990 | Wallsten ................. 606/191 X |
| 4,976,689 | 12/1990 | Buchbinder et al. . |
| 4,994,071 | 2/1991 | MacGregor ............. 606/192 X |
| 5,035,694 | 7/1991 | Kasprzyk et al. ........ 606/192 X |
| 5,040,548 | 8/1991 | Yock . |
| 5,089,005 | 2/1992 | Harada .................. 606/192 X |
| 5,108,416 | 4/1992 | Ryan et al. ............. 606/194 |
| 5,135,535 | 8/1992 | Kramer ................. 606/194 |

FOREIGN PATENT DOCUMENTS 0452901 10/1991 European Pat. Off. ............ 606/194

Primary Examiner—Randall L. Green
Assistant Examiner—Elizabeth M. Burke
Attorney, Agent, or Firm—Cowan, Liebowitz & Latman

[57] ABSTRACT

The invention relates to a rapid exchange catheter system comprising a exchange member having proximal and distal ends, the distal end of the rigid shaft being integral with the proximal end of the exchange member, such that said shaft is adapted to advance the exchange member distally to a desired location wherein the exchange member is positioned concentrically to a catheter shaft.

7 Claims, 3 Drawing Sheets

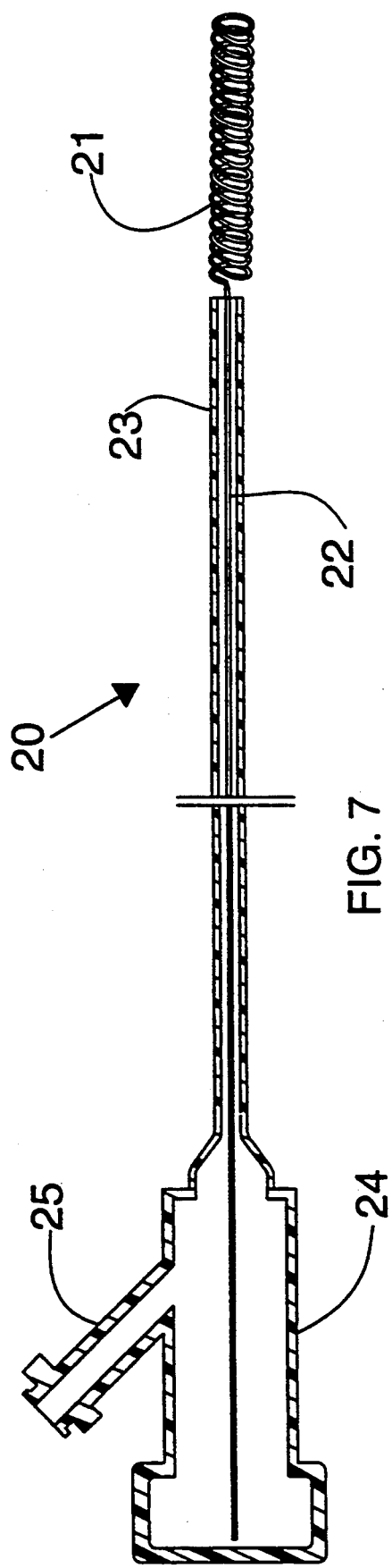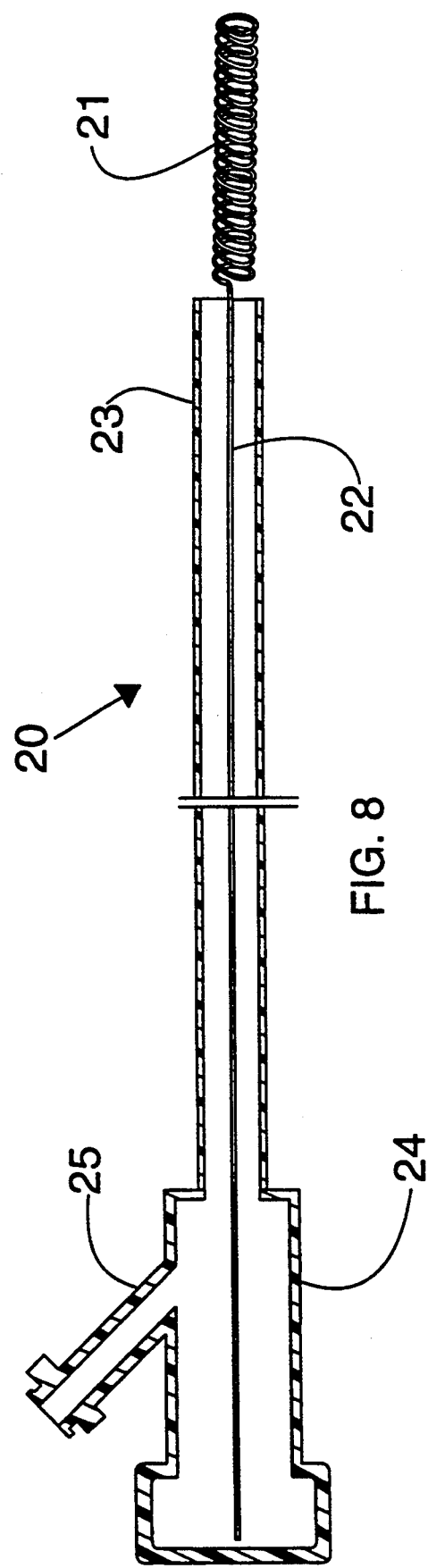

METHOD OF RAPID CATHETER EXCHANGE

CROSS-REFERENCE TO RELATED APPLICATION

This application is a divisional of co-pending U.S. patent application Ser. No. 07/859,220, filed Mar. 30, 1992.

FIELD OF THE INVENTION

This invention relates to a rapid exchange catheter system. More particularly, this invention relates to a rapid exchange catheter system comprising one or more balloon dilatation catheters and an exchange facilitator consisting of an elongated exchange member and a rigid shaft.

BACKGROUND OF INVENTION

In the utilization of catheters to diagnose and treat various medical disorders, it is very often required that more than one device be used during the procedure. Because positioning of the catheter at the desired location may be difficult, time consuming, or critical or pose a high risk, techniques have been developed that facilitate exchange of catheter devices.

The most common technique for catheter exchange employs a very long guidewire called an exchange wire. In this technique the exchange wire is placed within a central lumen of a catheter that has been previously positioned within the body. To maintain the desired position, the exchange wire is advanced while the catheter is simultaneously withdrawn. Once the catheter is completely out of the body, it is removed from the exchange wire. A second catheter is then positioned over the exchange wire, and, once the catheter is completely on the exchange wire, it is then advanced to the desired site in the body. This over-the-wire technique for catheter exchange is considerably time consuming, and it requires at least two operators to effect the exchange. In addition, the very long exchange wire extends beyond the sterile field, which adds to the risk of contamination during the procedure.

U.S. Pat. No. 4,762,129 to Bonzel and U.S. Pat. No. 5,040,548 to Yock describe balloon angioplasty catheters that can be exchanged over a standard length guidewire. These catheters are called monorail catheters, and they are designed such that only a relatively short segment of the distal end of the catheter is advanced over the guidewire, i.e., the catheter has a lumen to receive the guidewire that extends from the distal tip of the catheter to a location proximal to the balloon. Since the length of the guidewire used is only about half that of an exchange wire, the catheter exchange can be done more quickly, and a single operator may do the exchange. However, since a much shorter segment of the catheter is concentric to the guidewire, the monorail-type catheters have diminished axial support for tracking the guidewire (trackability) and transmission of axial or longitudinal forces (pushability).

In addition to the drawbacks cited above, both of the catheter exchange techniques described above have two additional shortcomings—increased diameter of the catheters to accommodate the guidewire, and risk of vessel trauma resulting from repeated catheter passages. In a number of applications, over-the-wire catheters are too large to be placed at the desired location. In these applications, smaller catheters, whose diameters have been reduced by eliminating the guidewire lumen, have been required. Exchange with these prior art systems consisted essentially of starting over after the first catheter was removed. This is often time consuming, and there is an increased risk of complications resulting from vessel trauma. U.S. Pat. Nos. 4,944,740 and 4,976,689 addressed the trauma issue by providing an outer tubular sheath concentric to an inner catheter. However, this system would have very limited application in small blood vessels, as the system itself would occlude the blood vessel and cause ischemic complications. Moreover, the outer tubular sheath must be used as a system with its inner catheter; if another catheter or guidewire was used initially, this system could not make the exchange.

OBJECTS OF THE INVENTION

It is an object of this invention to provide an atraumatic rapid exchange catheter system.

It is also an object of this invention to provide a rapid exchange catheter system comprising an exchange member and a pushing shaft.

It is a further object of this invention to provide a rapid exchange catheter system comprising an exchange member, a pushing shaft, an expandable sheath membrane, and a hemostasic manifold.

It is a yet further object of this invention to provide a method for the rapid exchange of exchange members, such as catheters, guidewires and other devices.

These and other objects of the invention will become more apparent in the discussion below.

BRIEF DESCRIPTION OF THE DRAWINGS

FIG. 7 represents an additional embodiment of the invention with the sheath collapsed;

FIG. 8 represents the embodiment of FIG. 7 with the sheath expanded; and

DETAILED DESCRIPTION OF THE INVENTION

Figure 1:
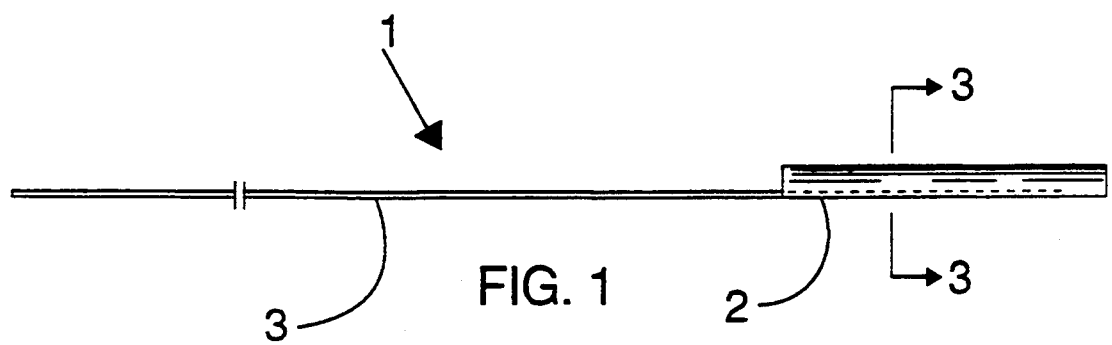
FIGS. 1 and 2 each represent lateral, longitudinal views of respective embodiments of the invention.

The rapid exchange catheter system (RECS) of this invention provides a very rapid, atraumatic means of exchanging one balloon dilatation catheter or other device for another balloon dilatation catheter or other device. The RECS is comprised of (1) a distal exchange member, preferably radiopaque, and (2) a rigid shaft or wire attached to the exchange member. Optionally the RECS may also comprise (3) a membrane sheath, which is folded around and attached along the length of the rigid shaft, and (4) a hemostatic manifold in fluid connection with the membrane sheath.

The RECS is used by, first, placing the exchange member over the proximal portion of the shaft of a catheter, e.g., a balloon dilatation (PTCA) catheter, or a guidewire or other device, that is to be withdrawn from a patient. Then, the exchange member is advanced distally along the shaft until the exchange member is positioned at the target site, i.e., adjacent to or across a stenosis, by pushing the rigid wire. The catheter, guidewire, or other device is withdrawn, and then, if a membrane sheath is present, the sheath is unfolded by flushing through the hemostatic manifold.

Now, subsequent PTCA catheters, guidewires, or other devices, for example, atherectomy catheters, laser catheters, stents, angioscopic or ultrasound imaging catheters, infusion catheters, perfusion catheters, or the like, may be passed through the sheath to the target site.

Additional exchanges can be made as desired through the sheath. Since such additional exchanges are made within the sheath, the subsequent catheters and other devices that are introduced do not rub against the intima of the arteries, as happens with both over-the-wire and monorail exchange techniques. The exchanges with the RECS are rapid and atraumatic, with the possibility of endothelial denudation, plaque, and intimal dissection minimized.

In addition to providing a rapid and atraumatic means for exchanging catheters and other devices, the RECS of the invention can also be used for subselective infusion and perfusion. Subselective infusion of various pharmacological agents directly to a lesion, especially during a procedure, may reduce complications, minimize systemic side-effects, and improve the long-term outcome of the procedure. In the event of an abrupt closure during an angioplasty, the RECS can be rapidly deployed to provide coronary perfusion. With the sheath in the collapsed, folded position, the distal exchange member can act as a temporary stent, providing passive perfusion. If necessary, blood or an oxygen-bearing fluid could be pumped through the sheath for active perfusion.

With the ability to perfuse, the RECS can provide lifesaving capability not presently available in known exchange systems. Patients can be stabilized, and the requirement of surgical standby for PTCA could be reduced or eliminated. In addition to significantly reducing the cost of a PTCA procedure, the reduction or elimination of the surgical standby requirement would facilitate increasing the number of PTCA procedures performed each year.

The invention can perhaps be better understood by making reference to the drawings. The embodiment of the invention 1 shown in FIG. 1 comprises an exchange member 2 and a rigid shaft, or corewire, 3 for advancing and/or retracting the exchange member 2 to and/or from the target area in the vasculature (not shown). The shaft 3 is preferably a wire. Exchange member 2 comprises a tubular member here; however, exchange member 2 can be comprised of any structure that defines a lumen suitable for exchange purposes.

Figure 2:
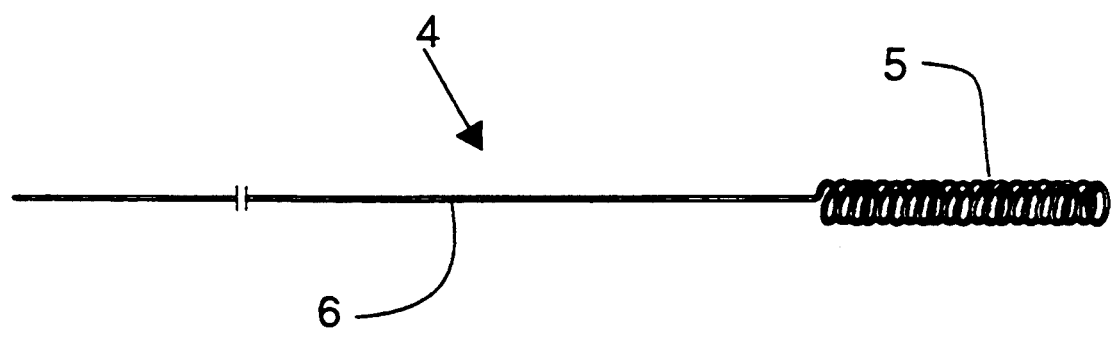

Another embodiment of the invention 4 can be seen in FIG. 2, wherein the exchange member is comprised of coil 5. Coil 5, which is preferably helically wound, is either continuous with shaft 6, that is, formed from the same wire, or is another wire attached to shaft 6, preferably by solder, glue, a weld, or similar affixation. In an alternate embodiment, coil 5 is butt joined to shaft 3.

Figures 3, 4, 5, 6:
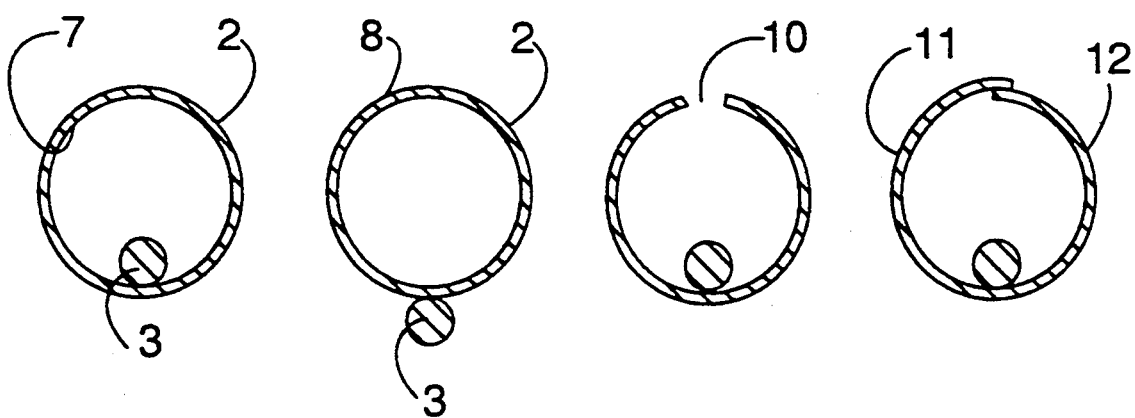
FIG. 3 represents a cross-sectional view of the embodiment of FIG. 1.
FIGS. 4, 5, and 6 represent additional cross-sectional views of embodiments of the invention.

FIG. 3 represents a cross-sectional view of exchange member 2, wherein it can be seen that shaft 3 is affixed to the interior surface 7 of exchange member 2. The distal portion of shaft 3 within exchange member 2 preferably extends at least about 25% of the length of exchange member 2, more preferably about 50 to 100% of the length of exchange member 2. It is within the scope of the invention that shaft 3 may extend distally of exchange member 2 and have, preferably, a flexible and/or otherwise atraumatic tip (not shown).

Shaft 3 may optionally, as shown in FIG. 4, be affixed to the outer surface 8 of exchange member 2, in the same manner as discussed for affixation to interior surface 7. It is also within the scope of this invention that shaft 3 could reside within the wall of exchange member 2.

As shown in FIG. 5, exchange member 2 may have a longitudinal slit 10 of sufficient width to enable the exchange member 2 to "snap" over a PTCA catheter, guidewire or other device. Preferably the width of slit 10 would be from about 1 to 5 mm. Also, as shown in FIG. 6, exchange member 2 may be discontinuous to the extent that wall members 11, 12 overlap to provide an opening of the same function as slit 10.

In a typical application of the invention described above, a PTCA catheter is in position across or adjacent to a stenosis. The exchange member 2 is positioned over the proximal end of the PTCA catheter outside the body, and the exchange member 2 is advanced over the PTCA catheter shaft to the stenosis. Then, the PTCA catheter is withdrawn, leaving the exchange member 2 across the stenosis, where it can function as a temporary stent to permit perfusion while additional therapy, for example, PTCA, atherectomy, insertion of a permanent stent, CABG, or the like, is planned. Optionally such an exchange can be done after the catheter/manifold hub of the PTCA catheter has been removed.

A secondary device, for example, a second PTCA catheter, is advanced adjacent to shaft 3, to the lesion. Then, the shaft 3 is moved proximally to cause exchange member 2 to move proximally, either adjacent to the target site or entirely from the body.

Rigid shaft 1 may be a conventional guidewire, preferably a spring guidewire, as is well known. Typical guidewires are shown in U.S. Pat. Nos. 4,757,827, 4,815,478, 4,813,434, 4,619,274, 4,554,929, 4,545,390, 4,538,622, 3,906,938, 3,973,556, and 4,719,924, all of which are incorporated herein by reference. In addition, shaft 3 could be solid or hollow, such as a hypotube, with an open distal end, to facilitate drug infusion. The proximal end of the shaft would then preferably have a Luer hub.

The shaft and exchange member of the invention may each optionally have a lubricous coating or covering, such as any of the known polysiloxane or TEFLON ® materials. Also, either, or both, of the shaft and exchange member could be made of lubricous material.

The exchange member is, in general, made of medically acceptable metal, for example, stainless steel, or rigid polymer, such as a polyester selected from the group consisting of polyurethanes, polyethyleneterephthalate, polyethyleneterephthalate glycol, and copolymers thereof, an olefin such as polyethylene or a copolymer thereof, polyvinylchloride, or the like. The exchange member could also be component of a material having properties (e.g., shape, size, or flexibility), that change due to hydration, temperature, or another factor. For example, a shape memory alloy such as Nitinol may be used.

It is within the scope of the invention that the exchange member may be detachable from the shaft, to leave the exchange member permanently in place. Such detachability could either be immediate or "on demand", where the shaft and exchange member would be joined in such a way, or with such a mechanism, that the operator could manipulate the proximal end of the shaft to cause the shaft and exchange member to separate. In the alternative, the shaft and exchange member may be affixed by appropriate glue, for example, whose adhesive properties would lessen with time, hydration, or temperature, such that after 24 to 48 hours the shaft could be detached and withdrawn. For example, the adhesive bonding properties of a hydrogel adhesive would diminish with hydration.

In the embodiment of the invention shown in FIGS. 7 and 8, the RECS 20 comprises a coil 21, preferably a radiopaque coil, and a rigid shaft or pushing wire 22. Positioned eccentrically or concentrically, preferably eccentrically, around shaft 22 is a flexible, collapsible sheath 23, shown collapsed in FIG. 7 and expanded in FIG. 8. At the proximal end of sheath 23 is a hemostatic manifold 24, including a valved infusion port 25 in fluid communication with the interior of sheath 23.

Figure 9:
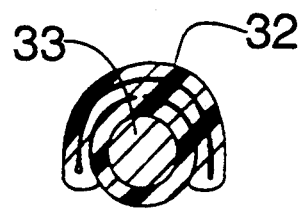
FIGS. 9 and 10 represent cross-sectional views of a further embodiment of the invention.
Figure 10:
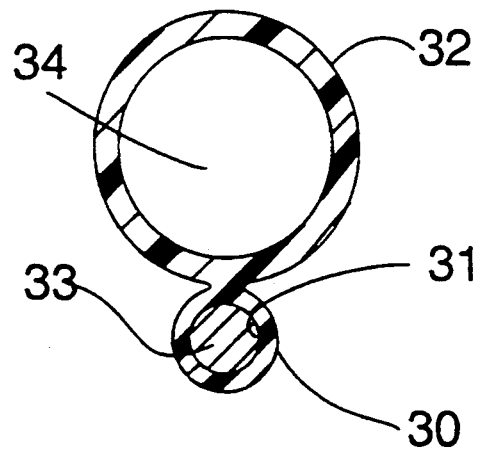

In the alternate embodiment shown in cross-section in FIGS. 9 and 10, sheath 32 is bonded or formed with shaft 30, which defines lumen 31. Pushing wire 33 extends longitudinally within lumen 31.

Sheath 23 or 32 extends distally to at least the distal end of pushing wire 22 or 33. Where exchange member 21 is instead a cylindrical tubular member, such as exchange member 2, the sheath 23 or 32 can extend into and/or through said exchange member.

Sheath 23 or 32 facilitates the passage of a second PTCA catheter, guidewire, or other exchangeable device after the first device is removed, and provides for atraumatic passage of these other devices since the sheath 23 or 32 prevents contact of the catheter or other device with the lining of the artery. Also, the sheath can provide a means for subselective catheterization for purposes such as (1) active perfusion of blood or oxygen-bearing fluid; (2) distal/selective dye injection; or (3) selective infusion of medications directly to the lesion site.

The flexible sheath 23 or 32 is preferably bonded by suitable means, such as heat-shrinking or adhesive, to the pushing wire 22 or 33, respectively, either continuously or at discrete points longitudinally along the pushing wire 22 or 33. The proximal end of the sheath 23 or 32 is bonded by suitable means, such as heat-shrinking or adhesive, to a manifold or hub, and the pushing wire 22 or 33 may terminate at the manifold or hub or extend proximally therethrough. Flexible sheath 23 or 32 and/or shaft 30 may each be single or multiple, such as double or triple, lumen.

The preceding specific embodiments are illustrative of the practice of the invention. It is to be understood, however, that other expedients known to those skilled in the art or disclosed herein, may be employed without departing from the spirit of the invention or the scope of the appended claims.

I claim:

1. A method of exchanging exchangeable members in a corporal channel, which comprises the steps of:
   (a) advancing into a patient's body a first exchangeable member having proximal and distal portions through a corporal channel so that the distal portion of said first exchangeable member is at a desired site;
   (b) placing an exchange member of a rapid exchange catheter system comprising:
      (1) an exchange member having proximal and distal ends, and
      (2) a rigid pushing wire having proximal and distal ends, the distal end of the pushing wire being integral with the proximal end of the exchange member, such that said pushing wire is configured to advance the exchange member distally to a desired location wherein the exchange member is positioned concentrically to an exchangeable member,
   over the proximal portion of said first exchangeable member and advancing said rapid exchange catheter system distally so that the distal portion of the exchange member is adjacent to or at the distal portion of the first exchangeable member;
   (c) withdrawing said first exchangeable member proximally through said exchange member and removing said first exchangeable member from the body;
   (d) advancing a second exchangeable member distally through said corporal channel through said exchange member to the desired site; and
   (e) withdrawing said exchange member through said corporal channel to remove the rapid exchange catheter system from the body.

2. The method of claim 1, wherein steps (c) and (d) are repeated at least one time.

3. The method of claim 1, wherein each exchangeable member is selected of the group consisting of catheters, balloon dilatation catheters, guidewires, stents, perfusion catheters, infusion catheters, and atherectomy catheters.

4. A method of exchanging exchangeable members in a corporal channel, which comprises the steps of:
   (a) advancing into a patient's body a first exchangeable member having proximal and distal portions through a corporal channel so that the distal portion of said first exchangeable member is at a desired site;
   (b) placing an exchange member of a rapid exchange catheter system comprising:
      (1) an exchange member having proximal and distal ends, and
      (2) a rigid pushing wire having proximal and distal ends, the distal end of the pushing wire being integral with the proximal end of the exchange member, such that said pushing wire is configured to advance the exchange member distally to a desired location wherein the exchange member is positioned concentrically to an exchangeable member, and wherein the pushing wire has a flexible, collapsible sheath having proximal and distal ends and being arranged thereon, such that as the collapsible sheath is expanded by infusion of fluid or insertion of a catheter, guidewire, or other device, the diameter of the sheath increases, and when the fluid flow ceases or the catheter, guidewire, or other device is withdrawn, the diameter of the sheath decreases,
   over the proximal portion of said first exchangeable member and advancing said rapid exchange catheter system distally so that the distal portion of the exchange member is adjacent to or at the distal portion of the first exchangeable member;
   (c) withdrawing said first exchangeable member proximally through said exchange member and removing said first exchangeable member from the body;
   (d) advancing a second exchangeable member distally through said corporal channel through said exchange member to the desired site; and
   (e) withdrawing said exchange member through said corporal channel to remove the rapid exchange catheter system from the body.

5. The method of claim 4, wherein steps (c) and (d) are repeated at least one time.

6. The method of claim 4, wherein the collapsible shaft inflates from fluid infusion or from insertion of said second exchangeable member.

7. The method of claim 4, wherein each exchangeable member is selected of the group consisting of catheters, balloon dilatation catheters, guidewires, stents, perfusion catheters, infusion catheters, and atherectomy catheters.

* * * * *